United States Patent

Yli-Urpo

Patent Number: 5,139,424
Date of Patent: Aug. 18, 1992

[54] IMPLANT FOR THE REPLACEMENT OF A TOOTH OR A PART OF THE BONE TISSUE

[76] Inventor: Antti Yli-Urpo, Värttinäkatu 17, Littoinen, Finland, SF-20660

[21] Appl. No.: 479,861

[22] Filed: Dec. 15, 1989

Related U.S. Application Data

[63] Continuation of PCT/FI88/00096, June 15, 1988

[30] Foreign Application Priority Data

Jun. 15, 1987 [FI] Finland .................... 872640

[51] Int. Cl.$^5$ .................................................. A61C 8/00
[52] U.S. Cl. .................................... 433/201.1; 623/16
[58] Field of Search ............... 433/173, 201.1; 623/16, 623/18; 128/60, 65, 67, 69, 72, 77

[56] References Cited

U.S. PATENT DOCUMENTS

| | | | |
|---|---|---|---|
| 4,146,936 | 4/1979 | Aoyagi et al. | 623/18 |
| 4,270,905 | 6/1981 | Mohammed | 433/201.1 |
| 4,483,678 | 11/1984 | Nishio et al. | 433/201.1 |
| 4,497,629 | 2/1985 | Ogino et al. | 433/173 |
| 4,599,085 | 7/1986 | Riess et al. | 433/201.1 |
| 4,725,234 | 2/1988 | Ethridge | 433/215 |
| 4,839,215 | 6/1989 | Starling et al. | 623/16 |
| 4,846,837 | 7/1989 | Kurze et al. | 623/16 |
| 4,904,264 | 2/1990 | Scheunemann | 623/23 |

FOREIGN PATENT DOCUMENTS 0006544 6/1979 European Pat. Off.
0023608 7/1980 European Pat. Off.
7614556-3 1/1981 Sweden.

Primary Examiner—John J. Wilson
Attorney, Agent, or Firm—Darby & Darby

[57] ABSTRACT

An implant for replacing a tooth or another part of bony tissue comprises a first non-resorbable layer (2) containing a bioglass, e.g., CaP-glass; a second layer (4) of a mixture of bioglass and hydroxyl apatite resorbable into bone or biomass, and a slowly resorbable intermediate layer (3) containing bioglass and being disposed between said first and second layers; the inclusion of said hydroxyl apatite into the second layer (4) securing the stability of bonding of the implant to the tissue. When strength is required, the implant further comprises a metal core (1) to which the first layer (2) is attached. The materials may also be used as a granule filler in bone cavities and as a block for the replacement of bone.

15 Claims, 3 Drawing Sheets

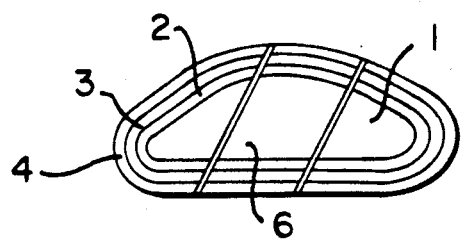
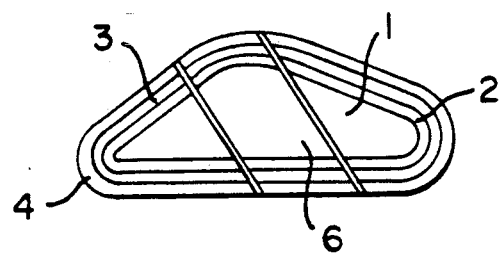
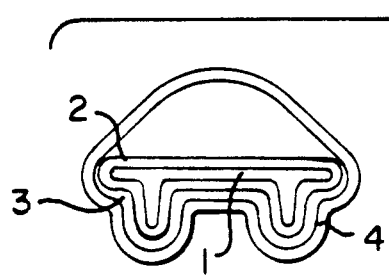
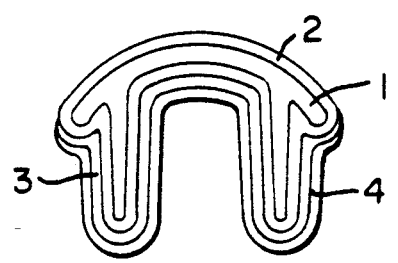
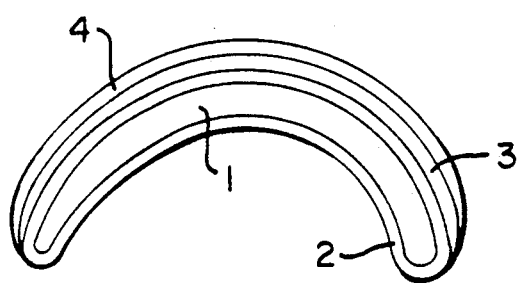
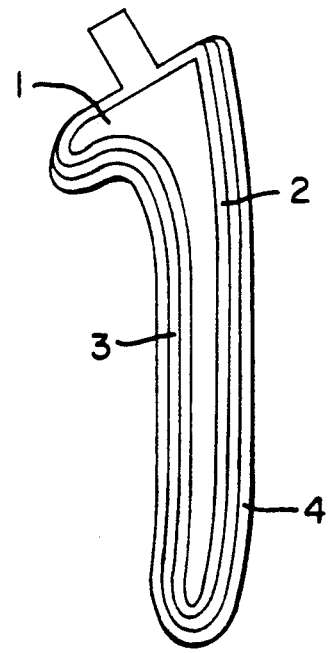
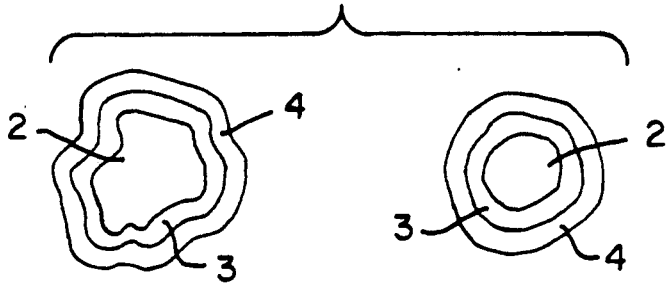

IMPLANT FOR THE REPLACEMENT OF A TOOTH OR A PART OF THE BONE TISSUE

This is a continuation of International Application No. PCT/FI88/00096, filed Jun. 15, 1988, which designated the U.S., and is now abandoned.

BACKGROUND OF THE INVENTION

The present invention relates to a tooth or bone implant, and more particularly, to a tooth or bone implant having three layers of varying resorbability.

The first attempts to place synthetic materials into the tissues were not made until the end of the eighteenth century, even though the subject has always been of interest to researchers. Those studies did not, however, bring about any satisfactory results. Instead, since the beginning of 1950's there has been varying success in placing titanium or tantalum metal blades into bone tissue, for example the jawbone.

Due to the difficulty of the necessary operation and the risk of infection, the large subperiosteal constructions and the large endosteal blades are becoming increasingly unpopular. These have been replaced by single screws (Brånemark, Straumann, Bioceram; ref. 1 Albrektson et al.; special reprint. The long term efficacy of currently used dental implants. A review and proposed criteria of success. Int. J. Oral and Max. Fac. Implants. 1. 1986.) and by large conical cylinders resembling a single tooth root. (Frialit; ref. 1.). For the present methods the structure is commonly placed into the alveolar bone. Thus it is possible to achieve a mechanical contact between the bone and the implant. The implant also penetrates the gingiva leaving a protrusion visible. This protrusion acts as a support for the protheses. To prevent bacterial invasion, it is necessary that the epithelium should attach closely to the surface of the protrusion. To achieve this, it is required to always keep the area clean.

The attachment of the implant to the bone in the above methods has often been prevented by an infectious tissue layer. It is possible to avoid this problem by a two stage operation technique in which the implant is totally screwed into the bone during the first stage (ad modum Brånemark, ref. 1.). After 3-6 months, the second stage is performed during which a protrusion is placed onto the implant. The results have been satisfactory.

Several variations of this method have been introduced (IK-implant, IMZ-implant, Core-vent-implant). The materials used are titanium or Co-Br alloy with Ti by plasma spraying (TiO$_2$). The healing period is between 3 to 6 months, even though the manufacturer promises a possibility of instant loading after operations. The main disadvantages are the difficulty and the complexity of the method.

Simpler, but less reliable, is the Straumann-method, in which the hollow perforated cylinder protrudes out of the gingiva and is placed into the bone with only one operation. The material is a Co-Cr alloy, which is coated with TiO$_2$ by plasma spraying. These cylinders were withdrawn from the market in 1986 due to their unreliability.

A third type of implant is the polycrystalline Al$_2$O$_3$-ceramic, Frialit-implant, which is placed directly after the tooth extraction into the widened root cavity. This implant narrows towards the end with distinct step. Because of the brittleness of the ceramic, these implant can only be used to support a single tooth which is subject to only small bite pressure, such as the front teeth.

The Japanese "Bioceram" Al-crystal-sapphire implant series by Kyoceran are implants that are smaller than the Frialit implant. These implants have a high value for other strength properties, but their ductility is low. Also the annealing has to be done carefully because of the brittleness of the material. The clinical results obtained do not correspond to the results given by the manufacturer. It appears that the bone attachment to Bioceram is not satisfactory. The reason for this is probably the inert nature and the low friction of the surface and the small surface area.

Even a long healing period does not seem to be enough to create a strong attachment.

The minimum dimensions of the bone required for the large and simple attaching mechanisms are a depth of 10 mm and a breadth of 5.5 mm (Straumann). After tooth extraction, the alveolar bone shrinks so much that there is seldom enough left for the placement of such implants.

Both the titanium (Ti) and the Al$_2$O$_3$ implants are too large, because the thin structure is not otherwise able to withstand the necessary mechanical stresses. In addition, the manufacture of Ti is difficult. On the other hand, the small implants (Brånemark) are complex and expensive, and the smallest, non-metallic (Bioceram) implants are brittle.

The material types used for tooth implants can be classified in the following way:
1. Non-biocompatible Metals, which are non-biocompatible: Co-Cr-alloys, stainless steels, Ni-alloys, noble metals of type IV (Indium, Holmium).
2. Inert materials, which do not react with the tissues but which obtain a close contact with the bone: Al$_2$O$_3$-ceramics, Ta- and Ti-metal, their alloys (TiV-4A16), carbon in its different forms, Teflon.
3. Biactive materials, which attach actively and quickly to the bone i.e. they are surface-reactive and induce bone growth:
   Hydroxyl apatite (HA), calcium phosphate glass (CaP-glass) and CaP-glass ceramics, "bioglasses".
   Tricalciumphosphate i.e. TCP (Resorbs i.e. dissolves into the tissue), The composition and the manufacturing method affects the resorption of these materials, and it varies from fully-resorbable to non-resorbable.

The following table represents the materials used in tooth implants and their properties.

| Material | 10 N/mm$^2$ Strength* | Bone bonding | Bonding to epithelium |
| --- | --- | --- | --- |
| Al-bioceramic material | 9–7/7–4 | ++ | ++ |
| Ca P-bioceramic material | 9–0.5/2–0.5 | ++ | ++ |
| Hydroxyl apatite | 0.5/0.5 | +++ | + |
| Titanium 99.9 | 6/5 | + | + |
| Ti—6 Al—4 V | 7/6 | ± | ± |
| Ti—6 Al—4 V + bioc. coat. | 7/6 | ++ | + |
| Steels | 9.75/7.5 | -- | -- |
| Co-alloys | 8.5/7 | − | − |
| Carbon | 5.5 | + | ± |
| Plastic (containing Ca) | 1–0.5 | ± | ± |
| Noble metal | 8.1/5.8–8.8/8.4 | ± | ± |

-continued

| Material | 10 N/mm² Strength* | Bone bonding | Bonding to epithelium |
| --- | --- | --- | --- |
| Tantalum | | + | - |

*tensile strength/fracture stress
- - - bonding to bone and to epithelium is very good and furthermore it induces bone growth.
+ + bonding to bone is very good
+ bonding to bone is good
± bonding to bone is not well defined
− there is no bonding
-- foreign particle reaction Current problems associated with biactive materials are as follows:

1. Joining hydroxyl apatite (HA) to metal is problematic. A mechanical joint has been attempted, but, because of the brittleness of HA and it has not led to satisfactory results. Also, plasma spraying has been attempted. However it has not been demonstrated that the crystal structure is conserved, and the surface is transformed to the easily resorbed TCP, so the joint is not durable (World High Tec. Congress, Milano 1986). Also, the coral-based (naturally occurring) HA has not provided any better results than the synthetic one. However, HA is a relatively inexpensive material, onto which collagen fibers of the tissues attach and mineralize very well (Jarcho et al. several studies; ref. 2 de Putter, de Lange, de Groot: *Permaucosal dental implants of dense hydroxyl apatite. Fixation in alveolar bone;* Abstract: Int. congress on tissue integration in oral and maxillofacial reconstruction, Brussels 1985).

2. CaP-glasses and glass ceramics, i.e. so called bioglasses, have been observed to obtain a good bone bonding (Hencke el al. 1971; ref. 3. Gross et Strung: *The interface of various glasses and glass ceramics with a bony implantation bed.* J. Biomed. Mat. Res. 251-271: 19, 1985).

The reaction is based on the creation of a $SiO_2$-rich layer and on the precipitation of Ca and P. Ca and P then crystallize into HA around the collagen fibers attached to the surface.

An ideal method of implanting a tooth prosthesis would fullfill the following requirements:

1. The implant must be small and strong and fully biocompatible:
   thus the elastic Ti and potentially allergic Ni- and Cr-alloys are not viable;
   remaining alternatives are sufficiently noble alloys (Au-, Pt-, Pd-alloys) or a hard Ti-alloy.
2. The implant must have a surface capable of bonding with bone and epithelium and it must have an enhancing effect on the bone growth.
   Such surfaces are:
   HA = Hydroxyl apatite
   TCP = Tricalcium phosphate
   Bioglass or glass ceramic At present there are implants that have a metal core in order to obtain a sufficiently small size and high strength. The core is coated with a bioglass (CaP-glass) which is non-resorbable due to its metal oxide content. In addition it has an outer layer, resorbable to bone or biomass, made of CaP-glass (ref. U.S. Pat. No. 4,497,629, Ogino et al.). Thus requirements 1 & 2 are superficially full-filled; however, as the outer layer is resorbed, the inner layer does not achieve a satisfactory bonding to the tissue.

SUMMARY OF THE INVENTION

The attachement of dental implants has been improved by using hydroxyl apatite (HA). According to the present invention, HA is used in the resorbable outer layer (resorbable CaP-glass + HA) and preferably also in the non-resorbable inner layer (non-resorbable CaP-glass + HA). In addition, the joining of these two layers is substantially enhanced with an intermediate layer, which has a CaP-glass of an adjustable resorption rate and which preferably contains HA.

More specifically the first non-resorbable layer contains 10 to 100 percent by weight of CaP-glass and 0 to 90 percent by weight of HA; the slowly resorbable intermediate layer contains 10 to 100 percent by weight of CaP-glass and 0 to 90 percent by weight of HA; and the second resorbable layer contains 10 to 99 percent by weight of CaP-glass and 1 to 90 percent by weight of HA.

The first layer can be made non-resorbable by adding a metal oxide or oxides thereto. Suitable metal oxides are oxides of titanium, aluminium, and zirconium. The first layer can also be made non-resorbable by varying the ratios between CaP, $SiO_2$ and/or $Na_2O$ in the CaP-glass.

In the following, an application of the invention, suitable for teeth, i.e. intraosteal implant, is explained in detail.

BRIEF DESCRIPTIONS OF THE DRAWINGS

FIGS. 3a, 3b, 3c and 3d represent a subperiosteal implant according to the present invention i.e. an implant placed between the bone and the periosteum.

FIGS. 4a, 4b and 4c represent a joint prosthesis according to the present invention.

FIGS. 5a, 5b, 5c and 5d represent an intraosteal granule filler placed in a bone cavity according to the present invention.

DESCRIPTION OF A PREFERRED EMBODIMENT

Figure 1:
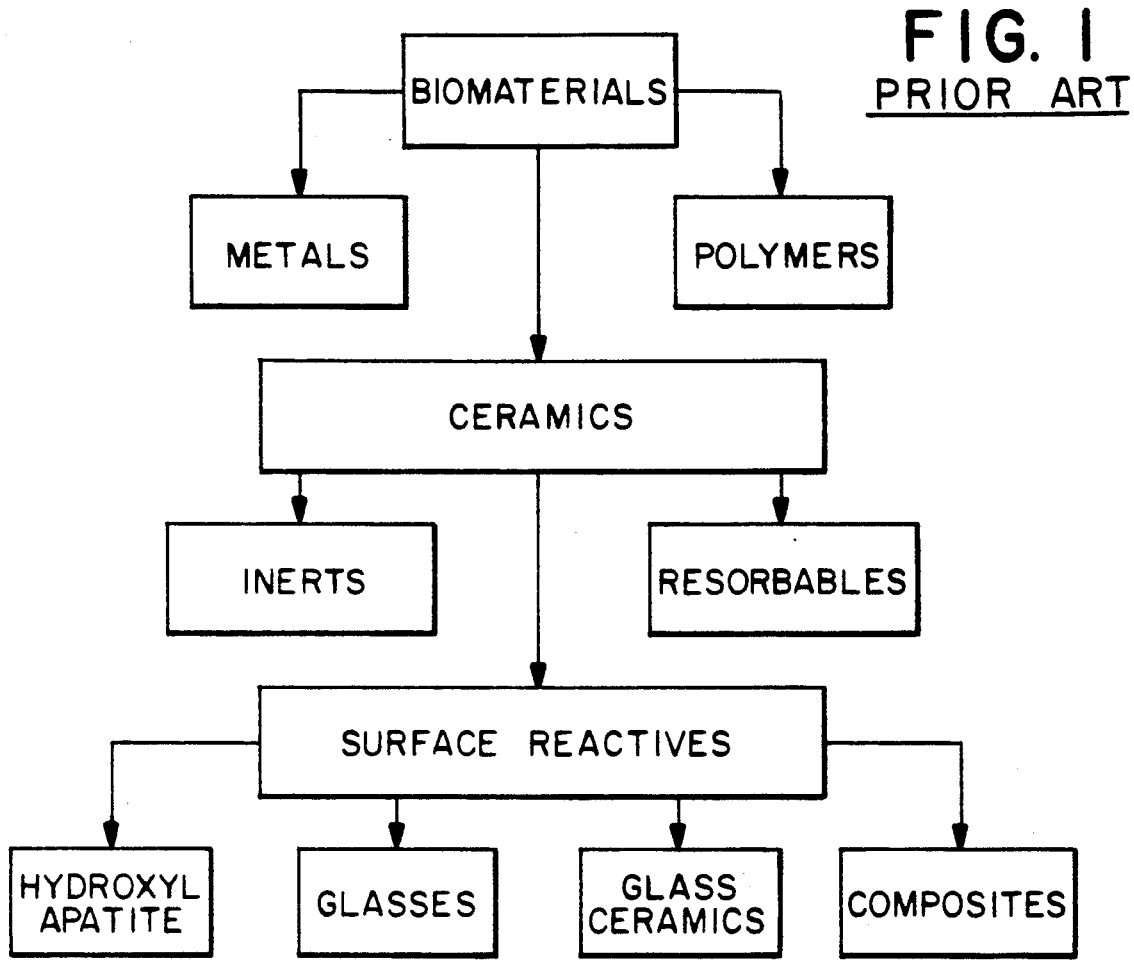
FIG. 1 represents the commonly used tooth implant materials.
Figure 2:
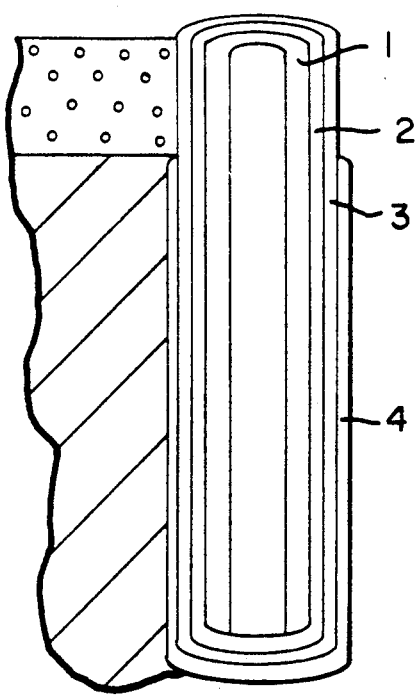
FIG. 2 represents a sample construction of the implant of the present invention.

A preferred embodiment of the implant according to the present invention comprises a: hard, surface oxidized metal core 1 (metal-to ceramic-alloys), with a thermal expansion coefficient of $10-15 \times 10^{-6}$/K, which is coated with a first (inner) layer of a strong, dense, and smooth non-resorbable bronzing bioglass, a mixture of CaP-glass and HA-ceramics 2, which has a smaller thermal expansion coefficient of $9-14 \times 10^{-6}$/K; which is coated with a second (intermediate) layer of a mixture of CaP-glass and HA 3, which is sintered to a dense or porous almost non-resorbable layer; which is coated with a third (outer) layer of a soft CaP-glass-HA mixture layer 4, which is resorbable, limits the bone interface, activates bone growth, and results directly in a mechanical bone to implant attachment without inducing excessive pressure on the bone.

The outer layer 4 can also be glazed when required. Thus the solution to the problem of the prior art is a layer structure, in which the outer layer 4 resorbs and the inner layer 2 closest to the metal core 1 does not. Thus the resorption cannot advance all the way to the metal surface, since layer 2 contains resorption prohibitors (e.g. metal oxides). Between layers 2 & 4 exists a semiresorbable interlayer. In addition, HA is added to all layers 2, 3 & 4 of Cap-glass. The joining of the layers (and HA) to the metal and to each other is strong and stable due to the glass. In particular it must be noted that HA is joined to the metal. In most cases, however, it is possible to achieve satisfactory stability, when the HA is not added to the, layer 2 on the surface of the metal, or when the CaP-glass-HA mixture layer 3 (intermediate layer) is excluded.

When a strong structure is not needed, the metal core is excluded. This is possible, for example, when the implant is used for bone augmentation.

The resorption rate of the glass/HA mixture is adjusted by controlling the proportion of ingredients in the composition and with additives (e.g. metal oxides) in the composition, just the rate of pure CaP-glass can be controlled. The CaP-glass/HA mixture surface of the invention attaches to the cells quickly (within 1-8 h) and the mineralization occurs quickly due to the presence of minerals in the implant. Such bone bonding is strong in weak bone structures because of the inductive effect of the materials on bone growth. Thus, this implant structure can be made smaller than prior art implants. In addition, the metal core supports the ceramic structure attached to it when needed. By glazing the surface, the advancing of the epithelium and loose connective tissue between the bone and the implant is prevented. Further applications of the invention can be obtained with different structures. These have been represented in the following table. There are other suitable compositions for the layers 2, 3, & 4:

the surface of the metal can have transverse grooves
the shape of the implant can be conical, cylindrical or threaded and its size can vary:
thickness e.g. 2.5-70 mm
length e.g. 7.0-700 mm
a ceramic cap can be placed on the top of the implant for the healing period
the implant can be embedded totally into the bone, under the periosteum or can be left partially outside the gingiva.

Other applications of the intraosteal implants according to the present invention are as follows:

1a). A subperiosteal implant placed between the periosteum and the bone.

Figure 3A:
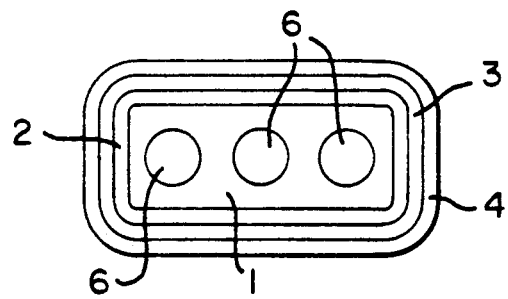
Figure 3B:
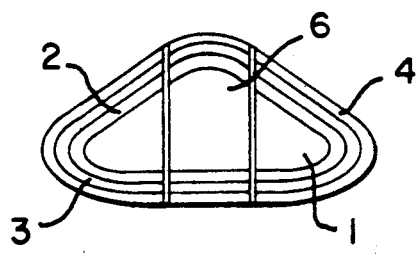

According to FIG. 3; the layers comprise:
1. metal
2. inert bioglass
3. HA/bioglass mixture
4. resorbable HA/bioglass mixture 2b). A joint prosthesis wherein the layers on the joint prostheses are the same as above and, further more, the joint surfaces are an inert dense base glass ceramics or metal.

The structure for in 1a and 1b is shown in FIG. 4; layers 1, 2, 3 & 4 are the same described above.

Figure 5B:
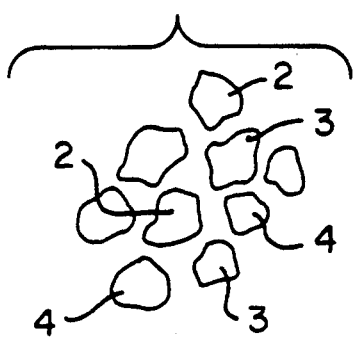
Figure 5C:
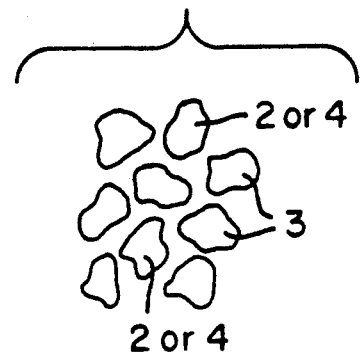
Figure 5D:
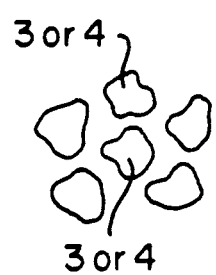

2. An intrasteal granule filling in bone cavities. This is shown in FIG. 5; layers 2, 3 & 4 are the same as described above. As filling 5 used large granules having a diameter between 1-5 mm, are used as follows:

a. the core of the granule is slowly resorbable, the surface quickly resorbable;
b. a part (2) of the granules are non-resorbable, a part (3) is slowly resorbable and a part (4) is quickly resorbable;
c. a part (3) of the granules are slowly resorbable and the rest of them (2) either quickly or non-resorbable (4);
d. part of the granules are either slowly (3) or quickly (4) resorbable.

3. A subperiosteal and periodontal granule filling as described above, but the granules are small and slowly resorbable. The diameter is between 0.1-1 mm and there are no layers.

In cases 2 and 3 there may be a hardenable plastic matrix which gives the desired shape according to the space.

Figure 6A:
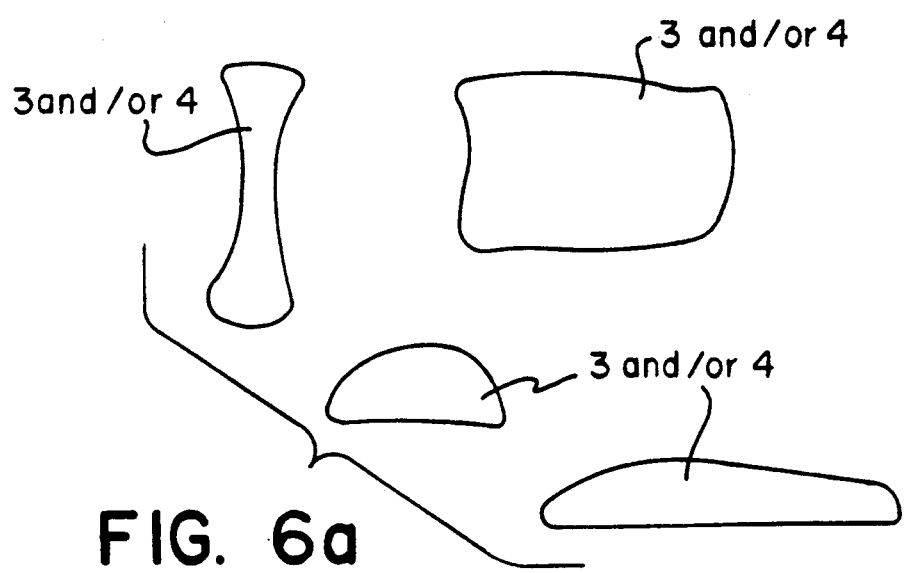
FIGS. 6a and 6b represent a bone-subsidy of bioceramic block according to the present invention.
Figure 6B:
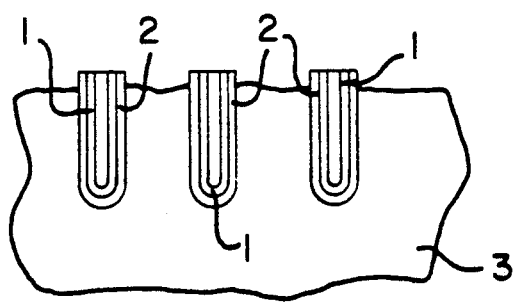

4. FIG. 6 represents an integrated alternative for granules; a bioceramic block for replacing bone. A block of ceramic can be made to be bone-bonding by having either a partially or totally slowly resorbable part 3 or quickly resorbable surface layer of CaP-glass/HA mixture as shown in FIG. 6a. The block can be preattached to metallic parts as shown in FIG. 6b. The block comprises slowly resorbable part 3 and the brazing layer of non-resorbable 2 CaP-glass/HA mixture material. In addition, the outer surface layer can be made of quickly resorbable material (4), if an enhanced bone bonding is desired.

What is claimed is:

1. An implant for replacing a tooth or another part of bony tissue comprising:
    a first inner non-resorbable layer containing a bioglass;
    a second outer layer of a mixture of bioglass and hydroxyl apatite resorbable into bone or biomass; and
    a slowly resorbable intermediate layer containing bioglass and being disposed between said first and second layers; the inclusion of said hydroxyl apatite into the second layer securing the stability of the bond between the implant and the tissue.

2. An implant according to claim 1, further comprising a metal core to which said first layer is attached.

3. An implant according to claim 1 or 2, wherein said first layer is made non-resorbable by the addition of a metal oxide or oxides thereto.

4. An implant according to claim 1, wherein the bioglass of the intermediate layer is calcium phosphate glass (CaP-glass) and is mixed with hydroxyl apatite.

5. An implant according to claim 1, wherein the bioglass of the first layer is calcium phosphate glass (CaP-glass) and is mixed with hydroxyl apatite.

6. An implant for replacing a tooth according to claim 1, further comprising:
    a metal core to which said first inner nonresorbable layer is attached, and wherein p1 the bioglass of said inner non-resorbable layer is calcium phosphate glass (CaP-glass) and the CaP-glass is mixed with hydroxyl apatite pattached to said metal core;
    the bioglass of said outer resorbable layer is CaP-glass and is mixed with hydroxyl apatite; and
    the bioglass of said slowly resorbable intermediate layer is CaP-glass and is mixed with hydroxyl apatite.

7. An implant used in joints, comprising:
    an inner resorbable layer including a mixture of and hydroxyl apatite;
    an outer non-resorbable layer containing bioglass; and
    a slowly resorbable intermediate layer including a mixture of bioglass and hydroxyl apatite; when the bone substance of the joint is inside the implant.

8. The implant of claim 7, wherein said bioglass is calcium phosphate glass.

9. A granule filler for use in bone cavities, said granules comprising:
   an inner non-resorbable layer containing bioglass;
   an outer resorbable layer including a mixture of bioglass and hydroxyl apatite; and
   a slowly resorbable intermediate layer including a mixture of bioglass and hydroxyl apatite; said granules being attachable to the bone and to each other as they are resorbed.

10. The granule filler of claim 9, wherein the bioglass is calcium phosphate glass.

11. A block for the replacement of bone which is at least partially made of a slowly resorbable mixture of calcium phosphate glass (CaP-glass) and hydroxyl apatite.

12. A block according to claim 11, further comprising metal parts attached to the block by means of a non-resorbable mixture of CaP-glass and hydroxyl apatite.

13. An implant for use in joints, comprising:
   an outer resorbable layer including a mixture of bioglass and hydroxyl apatite;
   an inner non-resorbable layer containing bioglass; and
   a slowly resorbable intermediate layer including a mixture of bioglass and hydroxyl apatite; when the bone substance of the joint is outside the implant.

14. The implant of claim 13, wherein said bioglass is calcium phosphate glass.

15. A block for the replacement of bone which is at least partially made of a quickly resorbable mixture of calcium phosphate glass (CaP-glass) and hydroxyl apatite, and metal parts attached to the block by means of a non-resorbable mixture of CaP-glass and hydroxyl apatite.

* * * * *